United States Patent [19]

Bauman

[11] Patent Number: 4,625,611

[45] Date of Patent: Dec. 2, 1986

[54] METHOD AND APPARATUS FOR REMOVING THE OUTERMOST LAYER OF A MULTILAYERED PRODUCT

[75] Inventor: Jack Bauman, Pacific Palisades, Calif.

[73] Assignee: General Medical Products, Inc., Santa Monica, Calif.

[21] Appl. No.: 721,561

[22] Filed: Apr. 10, 1985

[51] Int. Cl.⁴ .............................................. B26D 3/00
[52] U.S. Cl. ........................................ 83/861; 83/620; 83/870; 409/300; 409/303; 409/327
[58] Field of Search ............. 409/297, 326, 327, 330, 409/331, 345, 300, 303; 83/861, 870, 620, 697, 39, 622, 35

[56] References Cited

U.S. PATENT DOCUMENTS

| | | | |
|---|---|---|---|
| 1,361,215 | 12/1920 | Williams | 409/327 X |
| 1,382,193 | 6/1921 | Holmes | 83/620 X |
| 2,157,680 | 5/1939 | Spatta | 409/297 |
| 2,614,326 | 10/1952 | Loock | 409/326 X |
| 3,398,613 | 8/1968 | Gallotti | 409/300 |
| 3,399,585 | 9/1968 | Ahlert | 409/300 |

Primary Examiner—James M. Meister
Attorney, Agent, or Firm—Fulwider, Patton, Rieber Lee & Utecht

[57] ABSTRACT

This invention relates to a method and apparatus for removing a plurality of strips from the top or outermost layer of a multilayered product having a complex shape to expose a substrate having one or more properties substantially different from those of the top or outermost layer. The invention is particulary intended for use with a metal coated plastic support frame which may be used in the handle of an illuminating or examining device such as laryngoscopes. The support frame comprises a means to hold batteries, a light source and a switch, all integrally formed into a single structure. The apparatus and method of the invention are employed to electrically segregate areas of the metal coated support frame by removing strips of the metal coating.

12 Claims, 16 Drawing Figures

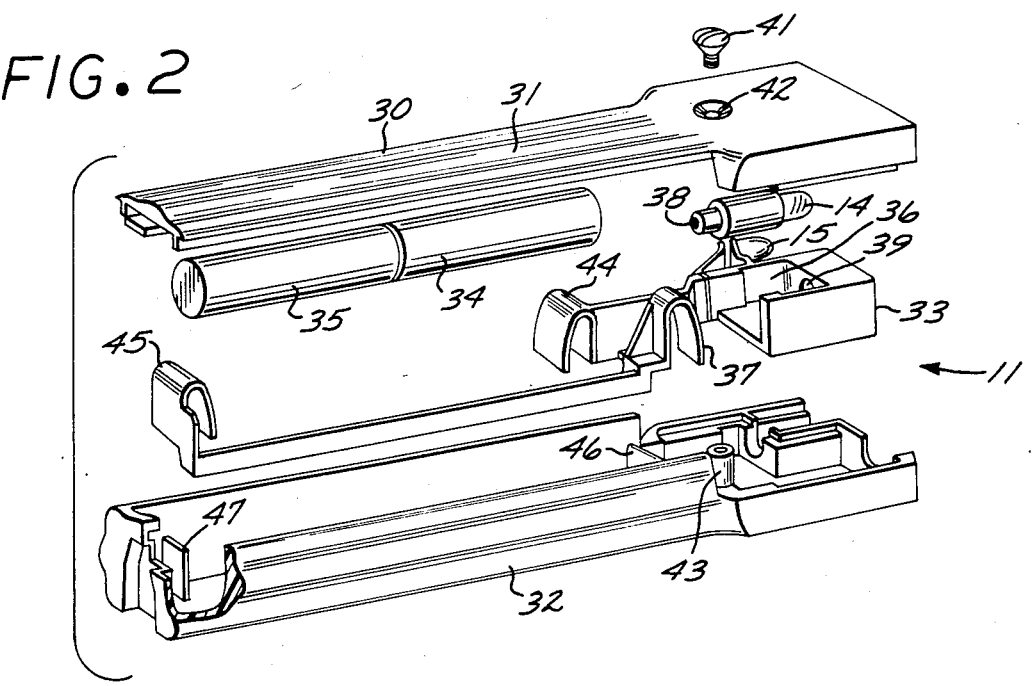
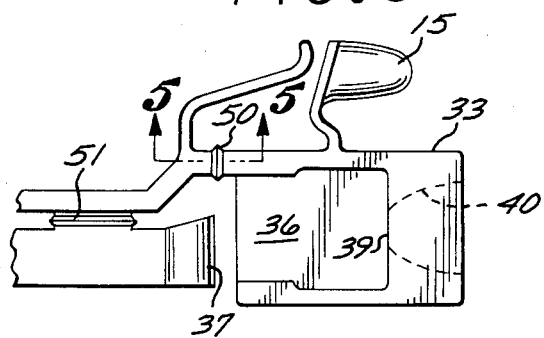
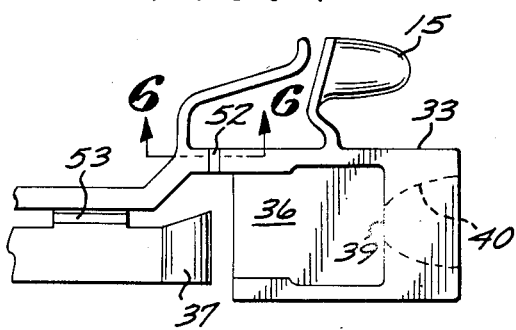
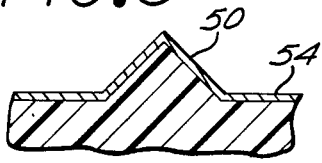
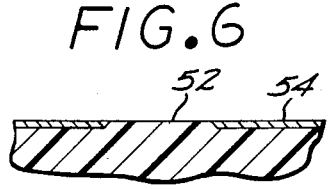
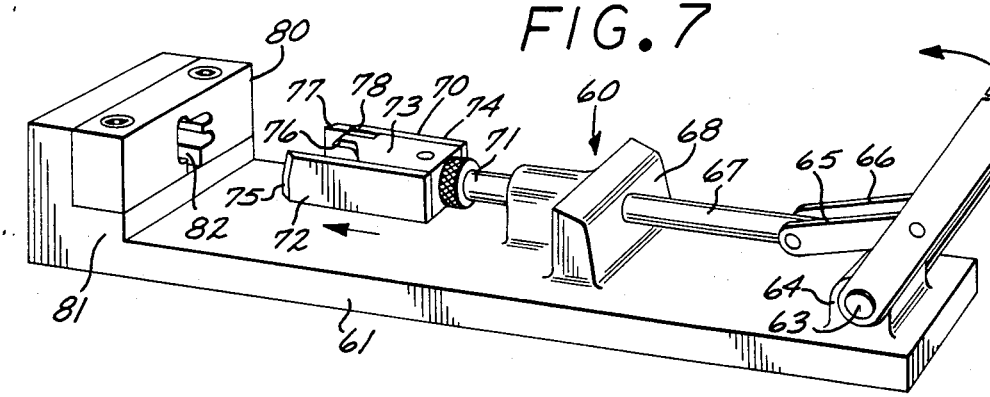

METHOD AND APPARATUS FOR REMOVING THE OUTERMOST LAYER OF A MULTILAYERED PRODUCT

BACKGROUND OF THE INVENTION

This invention relates to composite multilayered structures and particularly to a method and apparatus for separating the top surface of the multilayered product into discrete areas by removing strips of the top or outermost layer between the areas to thereby expose a substrate therebetween having substantially different properties than the top layer.

In the manufacture of complex composite structures which are adapted to conduct electricity over the surface thereof, the electrically conductive surface must be separated into electrically segregated areas so that the electrical current flows through only selected portions of the top surface in a desired manner. An example of such multilayered complex structures is described and claimed in the inventor's copending application Ser. No. 669,473, filed Nov. 8, 1984, which is directed to a metalized or metal plated plastic support frame suitable for use in illuminating or examining devices such as laryngoscopes having battery-operated, light generating means.

As described in the inventor's above-identified application, the support frame is a very complex structure which is formed by injection molding of a plastic material such as a platable grade of acrylonitryl-butadiene-styrene (ABS). After molding, the entire surface of the frame is plated one or more times with conductive metal and then strips of the metal coating are removed in order to electrically segregate areas of the plated top surface. Preferably, the frame is molded with ridges in those areas in which the plating is to be removed to electrically segregate the adjacent plated areas. This allows the ridges to be mechanically removed after plating and along with such ridge the metallized layer. The ridge removal exposes the underlying non-conducting substrate which electrically segregates the adjacent metalized areas.

Because of the complex structure of the frame and other similar structures, the manual removal of strips of the top metal layer is very tedious and time consuming. Moreover, such metal removal is subject to operator error in either not completely removing the metal between two discrete areas or removing metal from an area in which none should be removed.

There are presently no available simple devices which can readily remove strips of coating in the manner required by components having complex shapes. The present invention provides such a device and a method of removing such strips.

SUMMARY OF THE INVENTION

This invention is directed to a method and apparatus for removing strips or sections from the top or outermost layer of a multilayered structure having a complex shape to separate by such removal the surfaces on both thereof.

In accordance with the invention, a multi-layered product is held in a die or jig and its position therein fixed so that an operative head having a plurality of surface removing means and mounted on a driving means can be urged into engagement with the multilayered product so that the surface removing means, e.g., mutual blades, remove elongated strips of the top layer therefrom to thereby expose an underlying substrate having one or more properties which differ substantially from those of the top layer. In a preferred embodiment of the present invention, the top layer is electrically conducting whereas the substrate, which is exposed when the strip of the top layer is removed, is non-conductive or semiconductive so that the adjacent areas of the top layer are electrically segregated. By judiciously positioning the discontinuities in the top conductive layer, the flow of electricity can be controlled in a desired manner.

Multiple surface removing means, such as blades, are provided on the cutting head so that a plurality of strips can be removed from the top layer of the product in a plurality of planes when the head is urged against the multilayered product. The operative or cutting head is preferably mounted on a drive shaft which moves linearly with respect to the fixed multilayered product.

In order to properly position the multilayered product with respect to the cutting head, the product is first positioned in one die or jig which supports the part and fixes it with respect to the cutting head during the surface removing operations. After the first strip removal operation, the complex structure may be removed from the first die or jig and placed in a second die or jig to present a different side of the composite structure to another multibladed cutting head which can then be urged into engagement with the complex structure to remove strips of the top layer to create discontinuities therein as previously described.

The plurality of surface removing means on the operative cutting head are oriented so that strips of the top layer may be removed from a plurality of planes on the composite product. The cutting heads may be urged against two or more sides of the composite structure in order to remove continuous strips of the top layer to form discontinuities completely around portions of the product which separate sections of the product as desired or necessary, for example to control the electrical current flow on the surface thereof. To effectively control the electrical current flow, the metal layer must be removed down to the essentially non-conducting plastic substrate in the discontinuities.

The invention is described herein primarily as useful in removing strips from the outermost metallic layer ofa structure to expose a non-conducting substrate to thereby form a discontinuity therebetween. It is obvious that other embodiments may have different surface removing requirements. For example, the top surface of a particular complex structure may be non-conductive and the substrate exposed by the discontinuity between areas of the top layer may be electrically conductive.

The present invention provides a simple, inexpensive method for removing strips from the top layer of a composite multilayered product to expose a substrate having substantially different properties from the top layer and particularly to remove strips of the top or outermost layer from a plurality of planes on the product. These and other advantages of the invention will become more apparent from the following detailed description when taken in conjunction with the accompanying exemplary drawings.

BRIEF DESCRIPTION OF THE DRAWINGS

FIG. 2 is an exploded perspective view illustrating a laryngoscope handle with a multilayered unitary support frame adapted to fit within the handle;

FIG. 3 and 4 are top views of the support frame shown in FIG. 2 before and after strips of the top layer have been removed in accordance with embodiments of the invention;

FIG. 5 is a cross sectional view taken along the lines 5—5 shown in FIG. 3;

FIG. 6 is a cross sectional view taken along the line 6—6 shown in FIG. 4;

FIG. 7 is a perspective view of the an apparatus for removing strips of the top or outermost layer of a multilayered product which embodies features of the invention;

DETAILED DESCRIPTION OF THE INVENTION

Figure 1:
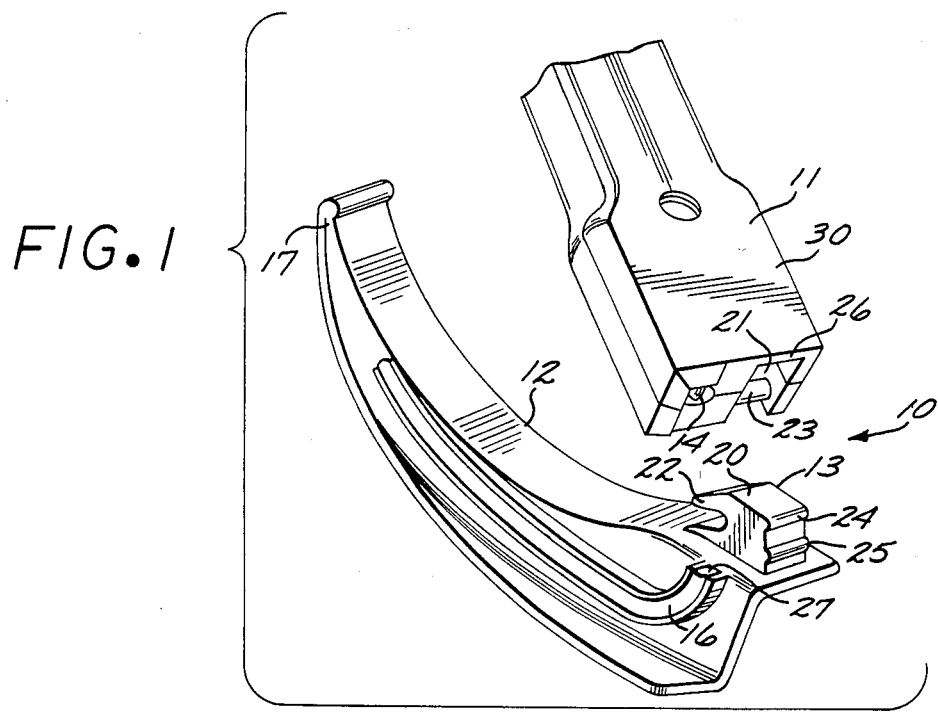
FIG. 1 is an exploded perspective view of the blade and handle of a laryngoscope which embodies features of the invention.

Reference is made to FIG. 1 which illustrates a laryngoscope 10 which generally comprises a handle 11, a detachable blade 12 and means 13 to detachably secure blade 12 to the handle 11 in a general L-shaped configuration. The laryngoscope handle 11 includes a light bulb 14 and a light switch 15 (not shown) to energize the light bulb 14. A light conductor 16 is provided in the blade 12 to transmit light to the distal end 17 of the blade 12 to facilitate observation.

The blade 12 is attached to the handle 11 by means 13 including appendage 20 which is inserted into the top channel 21 of the handle 11 with a pivotal motion so that the front end 22 of appendage 2o is hooked underneath the pivot rod 23 provided in the channel 21. When the blade is pivotally mounted onto the handle, the detents 24 and 25 engae a groove (not shown) in the back surface of wall 26 of the channel 21 to urge the appendage 20 into firm engagement with pivot rod 23 and to thereby fix the blade 12 with respect to the handle 11 in a generally L-shaped configuration with the light receiving face 27 of the light conductor 16 optically coupled to the light bulb 14.

With particular reference to FIG. 2, which is an exploded view of handle 11, a shell or housing 30 of handle 11 comprises a top section 31 which interfits with a bottom section 32. Also provided is a multilayered unitary support frame 33 which is secured within the bottom section 32. Support frame 33 is adapted to support batteries 34 and 35 and is provided with a cavity 36 which receives light source. Contact element 37 urges the light bulb 14 forward by pressing against the base terminal 38 so the light blub 14 passes through aperture 39 into the reflector 40. The frame 33 is also provided with a light switch 15 which is formed integral therewith. Shell 30 is formed by joining sections 31 and 32 by means of a screw 41 which passes through the opening 42 provided in section 31 and which is threaded secured to the upstanding post 43 fixed to the interior of section 32.

Unitary support frame 33 is secured within the lower section 32 by the back sides of electrical contact elements 44 and 45 thereof which snugly interfit with upstanding walls 46 and 47 repsectively.

The unitary support frame 33 is provided with a metal coating in order to conduct electricity between the batteries 34 and 35, the light switch 15 and the light bulb 14. Preferably, the surface of support frame 33 is first provided with an electrically conductve coating, such as copper, aluminum, silver or tin and then followed with a reflective coating of aluminum, silver chromium or nickle. From a manufacturing standpoint, it has been found very economical to plate the entire frame 33 with such conductive and reflective coatings and then remove strips of the coating in certain areas to form discontinuities in the conductive metallic coating in order to control the flow of electrical current in a desired manner.

In a preferred embodiment shown in FIG. 3 the support frame 33 is formed with ridges 50 and 51 in those areas where the discontinuities are desired to control current flow. After plating essentially the entire frame 33 with electrically conducting metal, the ridges 50 and 51 as shown in FIG. 3 are mechanically removed and with them the conductive coating, thereby leaving the desired discontinuities 52 and 53 as shown in FIG. 4. FIGS. 5 and 6 illustrate respectively a portion of the frame 33 before and after the ridge 50 and thus metal layer 54 is removed.

FIG. 7 illustrates an apparatus 60 for removing a plurality of strips from the top layer of a multilayered product such as frame 33 having a complex shape which incorporates embodiments of the invention. The apparatus 60 comprises a base 61, a handle 62 rotatably mounted on the base by means of a shaft 63 journaled in housing 64 which is an integral part of the base 61. Arms 65 and 66 are rotatably interconnected with both the handle 62 and a drive shaft 67 which is mounted in a housing 68 formed integral with the base 61. Operative cutting head 70 which is fixed to the distal end 71 of the drive shaft 67 is provided with a plurality of surface removing means or blades 72, 73 and 74. Blade 72 is provided with cutting surface 75, blade 73 with cutting surface 76 and blade 74 with curring surfaces 77 and 78.

Figure 8:
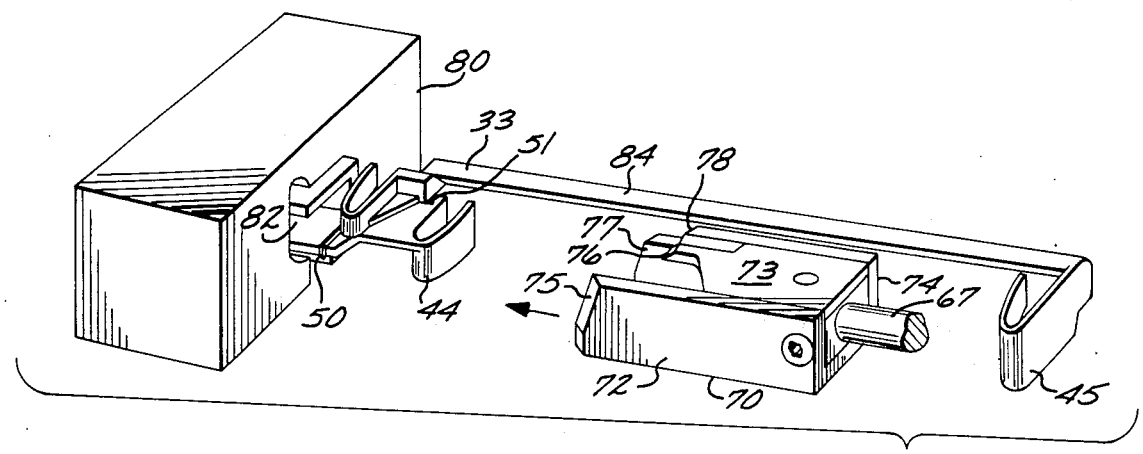
FIG. 8 is a partial perspective view of the trimming apparatus shown in FIG. 7 with the unitary support frame positioned within the die cavity.
Figure 10:
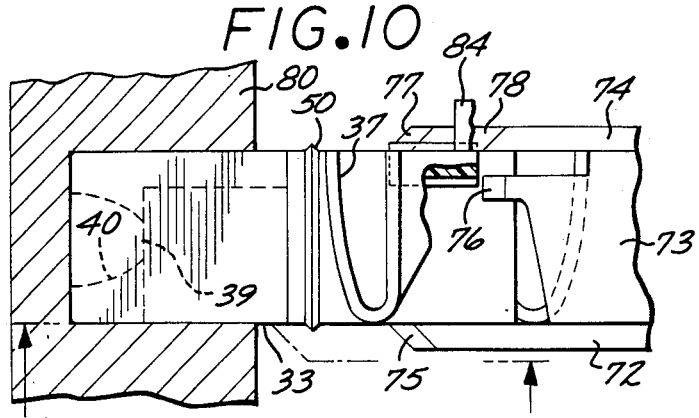
FIG. 10 is a top view partially in section of a unitary support frame shown in FIG. 2 mounted in the die cavity of the apparatus shown in FIG. 7.
Figure 12:
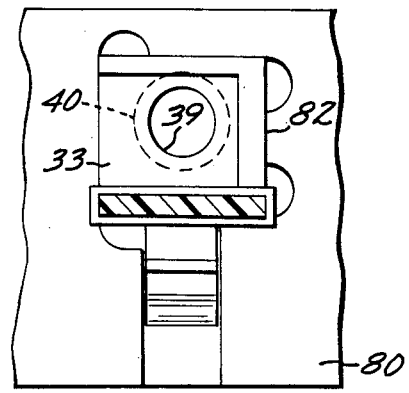
FIG. 12 is a sectional view taken along the lines of 12—12 shown in FIG. 11.
Figure 11:
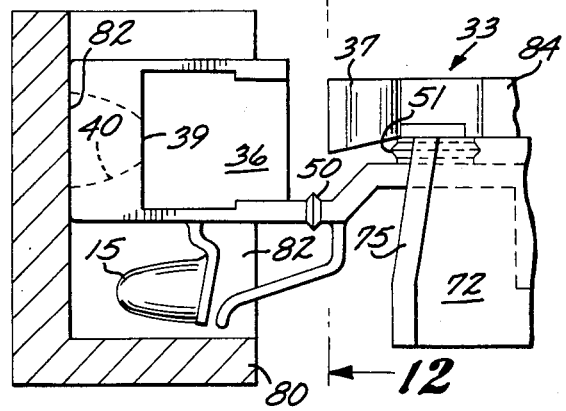
FIG. 11 is a side view partially in section of the view taken along the lines of 11—11 shown in FIG. 10.
Figure 13:
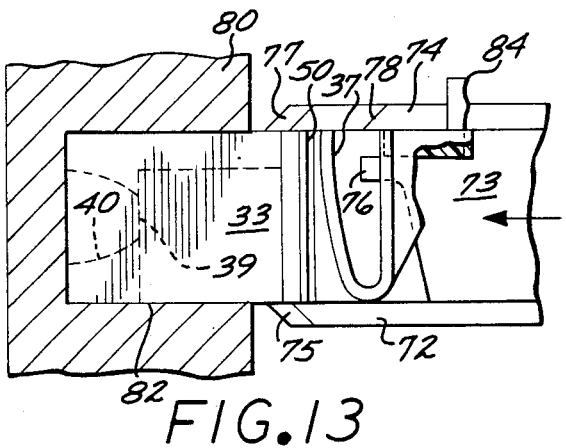
FIG. 13 is a top view similar to the view shown in FIG. 10 except that the cutting head of the apparatus has been moved forward to remove the ridges on the unitary support frame.

Die member 80 is fixed to a die support element 81 on base 61 and is provided with a die cavity 82 which is shaped to hold the complex composite structure of frame 33 in a fixed position with respect to the cutting head 70. As shown in more detail in FIGS. 8 and 10, frame 33 is positioned within the die cavity 82 with the light switch 15 oriented downwardly and the elongated leg 84 of the frame 33 extending outwardly therefrom. By pushing the handle 62 forward as shown in FIG. 7, the cutting head 70 is driven forward toward the frame 33 fixed within the die cavity 82 as shown in FIG. 10. The cutting surfaces 75 and 77 of blades 72 and 74, respectively first engage then remove the short portions of plated ridge 50. As the cutting head 70 continues its forwardmovement, the cutting surfaces 76 and 78 of the blades 73 and 74 respectively, engage and then remove the long portion of the plated ridge 51 as shwon in FIG. 13.

Figure 9:
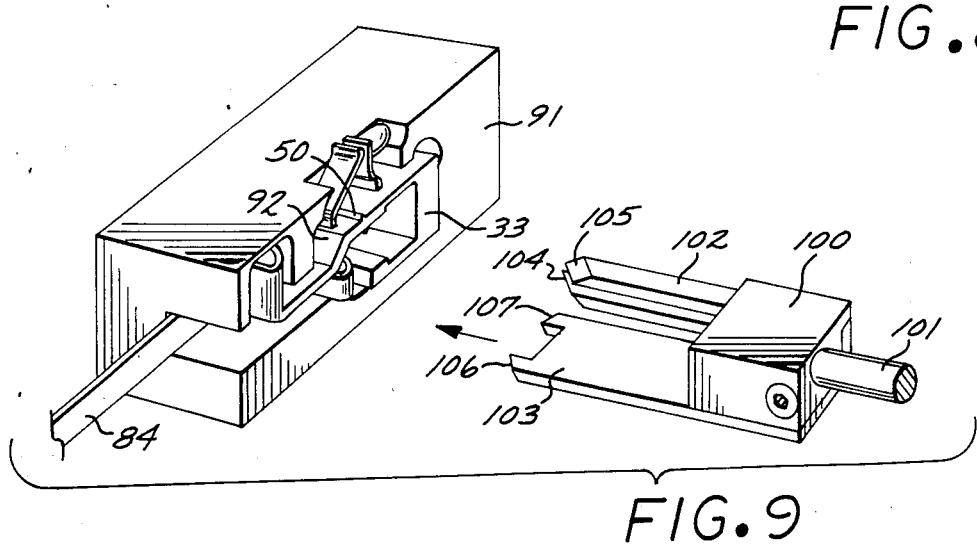
FIG. 9 is a partial perspective view of an apparatus similar to that shown in FIGS. 7 and 8 but with a different die and operative cutting head and showing a unitary support frame positioned within the die cavity.
Figure 14:
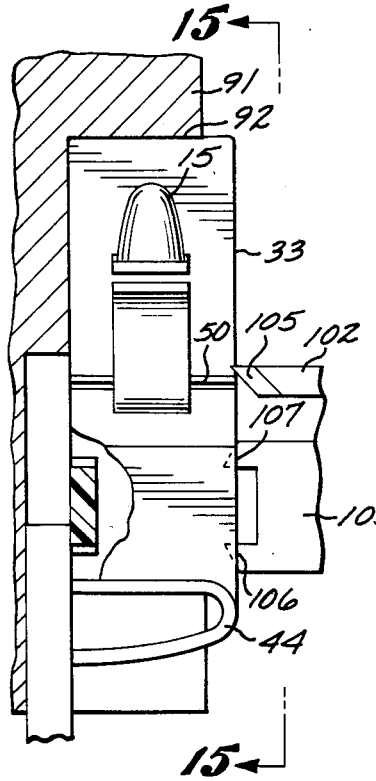
FIG. 14 is a top view partially in section of the support frame mounted on the cavity of the die shown in FIG. 9.
Figure 15:
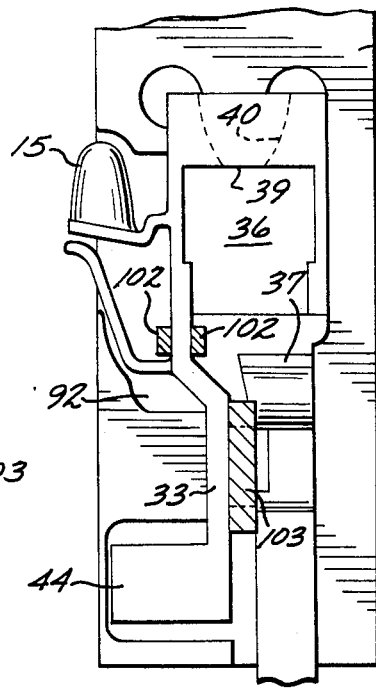
FIG. 15 is a front view taken along the lines of 15—15 shown in FIG. 14.
Figure 16:
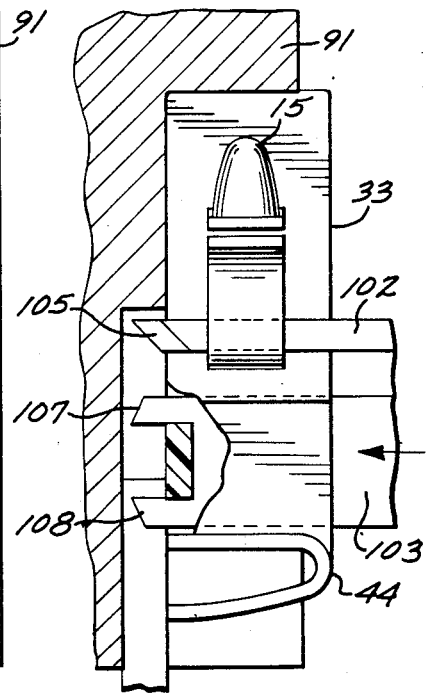
FIG. 16 is a top view shown in FIG. 14 except that the cutting head of the apparatus has been moved forward to remove the ridges on the frame.

The cutting head 70 is pulled away from the die 80 by pulling on the handle 62. The partially trimmed frame 33 is withdrawn from the die cavity 82 and placed into the die cavity 92 of second die member 91 as shown in FIG. 9 mounted on a separate base (not shown) essentially identical to the base 61 of the apparatus shown in FIG. 7. To orient the multilayered frame 33 to fit into the cavity 92 the frame 33 is rotated 180° about its longitudinal axis so the light switch 15 extends upwardly and the leg 84 of the frame 33 is rotated 90 degrees to the left from the orientation shown in FIG. 8. The cutting head 100 mounted on drive shaft 101 of the second trimming apparatus is provided with a plurality of blades 102 and 103 and each of the blades have cutting surfaces 104, 105 and 106, 107 respectively. The cutting head 100 is thrust forward toward the frame 33 fixed within the die 91 by pushing on a handle (not shown) as was the case with the first trimming apparatus shown in FIG. 7. The two cutting surfaces 104 and 105 of the vertically oriented side blade 102 first engage and then remove the long sides of plated ridge 50 as shown in FIGS. 14 and 15. As the cutting head 100 continues its forward motion of the cutting head the cutting surfaces 106 and 107 of the horizontally oriented blade 103 engage and then remove the short sides of plated ridge 51 as shown in FIG. 16. In this manner both ridges 50 and 51 which encircle portions of frame 33 are completely removed to expose a non-conducting substrate and to thereby electrically segregate portions of the frame 33.

The completely trimmed multilayered frame 33 is then removed from the die cavity 92 and may be then installed in the handle 11 of a laryngoscope as shown in FIG. 2.

Although the trimming apparatus of the present invention as described and shown herein are hand operated devices, it is to be understood that these devices can readily be designed by those skilled in the art to be automatically operated. Additionally, while blades described herein shave or skive the top coating layer, other layer removing means can be employed such as rotating abrasive elements. The apparatus can be used for surface removal in a wide variety of three dimensional instruments and devices. Other modifications and improvements can be made to the present invention without departing from the concepts thereof.

I claim:

1. A method of removing a plurality of strips from the outer layer of a multilayered product which has a substrate with at least one property substantially different than the same property of the outer layer, comprising:
   a. holding the multilayered product in a first position with respect to an operative head having a plurality of surface removing means;
   b. moving the operating head into engagement with the multilayered product in the first position to remove a plurality of strips of the outer layer of the multilayered product and thereby to expose strips of substrate having at least one property which is substantially different than the same property of the outer layer thereof;
   c. disengaging the operative head from the multilayered product;
   d. holding the multilayered product in a second position with respect to an operative head having a plurality of surface removing means; and
   e. moving the operative head into engagement with the multilayered product in the second position to remove additional strips of the outer layer from the multilayered product to expose additional strips of said substrate.

2. The method of claim 1 wherein the product has surfaces located in a least two different planes and surface removing means are oriented to remove strips from at least two different planes on the surface of the product.

3. The method of claim 1 wherein the strips of the outer layer are removed by blades which shave or skive the outer layer.

4. The method of claim 1 wherein the angular change in the orientation of the multilayered product when changing from the first position to the second position is 90° or a multiple thereof in either a horizontal or a vertical plane.

5. The method of claim 1 wherein the movement of the one or more operative heads into engagement with the multilayered product is linear.

6. The method of claim 1 wherein the multilayered product is held in a first die or jig while a first operative head removes a plurality of strips from the outer layer of the product and held in a second die or jig while a second operative head removes a plurality of strips from the outer layer of the product.

7. The method of claim 1 wherein at least one of the strips removed from the product in the first position and at least one of the strips removed from the product in the second position expose a continuous strip of substrate.

8. An apparatus for removing a plurality of strips from the outer layer of a multilayered product which has a substrate with at least one property substantially different than the same property of the outer layer, comprising:
   a. a means to hold the multilayered product in a first position;
   b. one or more operative heads having a plurality of surface removing means;
   c. means to urge one of the operative heads into engagement with the multilayered product in the first position to remove strips of the outer layer thereof;
   d. means to hold the multilayered product in a second position of different orientation than the first position with respect to the operating head which is to be urged against the product in that position; and
   e. means to urge one of the operative heads into engagement with the multilayered product in the second position to remove strips of the multilayered product.

9. The apparatus of claim 7 wherein the means to urge the operature head into engagement with the multilayered product includes a means to drive the operative head toward and away from the said product in a linear manner.

10. The apparatus of claim 8 wherein the means to hold the multilayered product in a fixed position is a die or jig.

11. The apparatus of claim 9 wherein the operative head is fixed to the distal end of a drive shaft.

12. The apparatus of claim 11 wherein the means to drive the operative head fixed to the distal end of the drive shaft is a handle rotatably mounted on a support base and connected to the proximal end of the drive shaft so that the drive shaft may be moved in a linear fashion by moving the handle.

* * * * *